United States Patent [19]

Held

[11] Patent Number: 5,618,258
[45] Date of Patent: Apr. 8, 1997

[54] THUMB RING FOR AN ENDOSCOPIC APPARATUS

[75] Inventor: Manfred Held, Hamburg, Germany

[73] Assignee: Olympus Winter & Ibe GmbH, Hamburg, Germany

[21] Appl. No.: 607,836

[22] Filed: Feb. 27, 1996

[30] Foreign Application Priority Data

Mar. 25, 1995 [DE] Germany .................. 195 11 092.7

[51] Int. Cl.⁶ .................................................. A61B 1/31
[52] U.S. Cl. ............................................................ 600/104
[58] Field of Search ............................... 30/231–232, 298;
81/177.1, 177.3; 600/104–106, 131; 606/45–46,
140–141, 205; D24/137–138, 143

[56] References Cited

U.S. PATENT DOCUMENTS

| 25,140 | 7/1859 | Roome | 30/251 |
|---|---|---|---|
| 2,669,992 | 2/1954 | Curutchet | 606/205 |
| 2,669,993 | 2/1954 | Curutchet | 606/205 |
| 3,727,605 | 4/1973 | Klein | 600/131 |
| 4,137,920 | 2/1979 | Bonnet | 606/171 |
| 4,250,873 | 2/1981 | Bonnet | 600/104 |
| 5,112,329 | 5/1992 | Storz | 606/46 |
| 5,423,795 | 6/1995 | Eckert et al. | 606/1 |

FOREIGN PATENT DOCUMENTS 2649634  1/1991  France ................... 30/232

Primary Examiner—Jerome Donnelly
Assistant Examiner—David R. Risley
Attorney, Agent, or Firm—Walter C. Farley

[57] ABSTRACT

A thumb ring for an endoscopic instrument is rotatably mounted at an affixation site to be rotatable about an axis parallel to the instrument longitudinal axis. A thumb insertion aperture has a concave rest surface in the ring opposite the affixation site. The rest surface is substantially shaped like a cylinder segment of which the axis, as seen in the direction of thumb insertion, forms an acute angle with the ring axis.

2 Claims, 2 Drawing Sheets

THUMB RING FOR AN ENDOSCOPIC APPARATUS

FIELD OF THE INVENTION

This invention relates to a thumb ring for controlling motion of operating parts of an endoscopic device.

BACKGROUND OF THE INVENTION

Thumb rings of this general type are used especially in those endoscopic devices comprising medical instruments actuated with one hand. Illustratively, such may be resectoscopes operating with a high-frequency driven cutting loop, but also they may be optical urethrotomes or the like.

As a rule, a thumb ring for this kind of apparatus constitutes that part of a handle with which the medical instrument is actuated in a one-handed manner. The other part comprises a mating grip mounted on the instrument at a gripping distance from and distally from the thumb ring. Almost always, the thumb ring is affixed at one site of the instrument so as to be rotatable about an axis which is parallel to the longitudinal instrument axis. As a result, the surgeon may freely select that angular position of the thumb ring which is convenient for him.

The medical instrument is operated by relatively displacing the thumb ring and the mating grip in an axial direction relative to the instrument axis. Accordingly, as regards the known endoscopic implements, either the thumb ring or the mating grip may be stationary while the other part of the grip is then movable.

In order to hold the instrument, the surgeon inserts his thumb into the thumb ring and by means of at least one of the remaining fingers seizes the mating grip which usually comprises two grip components laterally projecting from the instrument. The surgeon can reliably hold the instrument by one hand and also (again one-handedly) he can actuate the medical instrument therein. To provide the surgeon with adequate actuating reliability, however, the thumb must be relatively firmly affixed into the thumb ring. Only then is it possible for the surgeon reliably to hold the instrument and only then can the handle be driven with adequate accuracy. But conventional thumb rings may press into the sensitive top thumb side in this process and cause painful pressure. The surgeon may be unpleasantly affected during and after prolonged use of the instrument.

SUMMARY OF THE INVENTION

Accordingly, an object of the present invention is to provide a thumb ring for endoscopic instruments allowing pain-free seating of the thumb even after prolonged instrument use.

Briefly described, the invention comprises a thumb ring for an endoscopic instrument with a generally annular body having a passage therethrough with a central axis, the passage having two ends, at least one end being usable as an insertion aperture for inserting a thumb of an operator through the passage. One side of said body is mounted on an endoscopic instrument so that the body is rotatable about an axis parallel with an instrument longitudinal axis. A concave rest surface is formed on the passage adjacent the insertion aperture end on a side of the ring opposite the rotatably mounted side, the concave rest surface substantially being in the form of a segment of a cylinder having an axis of revolution, as seen in the direction of insertion of the thumb slanting toward the axis of the ring.

Thus, the thumb ring of the invention comprises at least one concave rest surface for the top side of the thumb and associated with one of the two apertures and located opposite the affixation site. Substantially this rest surface corresponds to a cylinder segment of which the axis as seen in the direction of thumb insertion slants relative to the ring axis.

A thumb ring is made in this manner which, unlike conventional thumb rings, will not rest against the top side of the thumb along a line, but makes contact over an area with said side. Consequently the pressure on the thumb top side is spread out and the painful stress on it is avoided or at least decreased.

The slope of the rest surface must be selected to substantially correspond to that of the area of contact of the thumb top side in the operating position. Only in this way is it possible to assure the largest possible contact area between thumb and rest surface. The appropriate slope of the rest surface may be easily and empirically determined (or also computed) by the expert before manufacturing the particular thumb rings.

As already discussed above, the thumb rings of conventional endoscopic implements are rotatably supported on a shaft parallel to the longitudinal instrument shaft or even on same. In conventional rings, both apertures may be used as insert apertures. In order to secure the same feature in the thumb ring of the invention, an advantageous embodiment provides that one rest surface be associated with each thumb-ring aperture. Independently of which aperture is selected by the surgeon to insert his thumb, the thumb ring of this embodiment in each case offers an advantageous rest surface.

It was already stated that the rest surface essentially assumes the shape of a cylinder segment. This concept is to be construed broadly and includes rest surfaces for instance which, seen in the direction of the axis of the cylinder evince a slight convex bulge. This design accounts for the fact that the thumb top-side in the rest zone (approximately the middle third of the small finger) when seen in the direction of the longitudinal thumb axis is not rigorously straight but almost always will be curved somewhat concavely. If the said rest surface is made slightly convex, especially good area-contact is achieved with the thumb top side.

BRIEF DESCRIPTION OF THE DRAWINGS

The invention is described in greater detail hereinafter with reference to the following drawings wherein.

DESCRIPTION OF THE PREFERRED EMBODIMENTS

Figure 1:
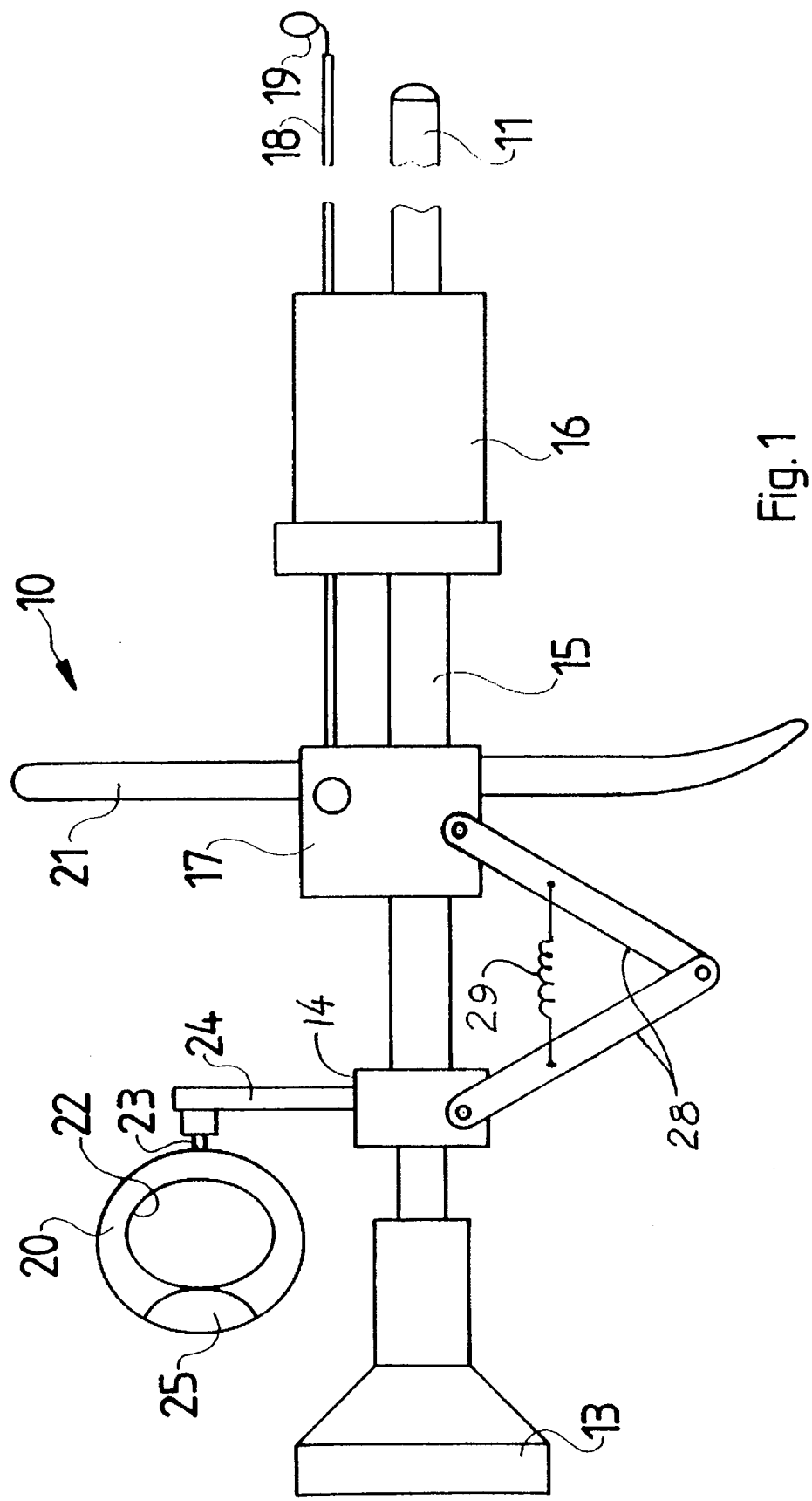
FIG. 1 is a schematic side elevation, partly foreshortened, of a conventional resectoscope fitted with a thumb ring in accordance with the invention.

FIG. 1 shows a resectoscope 10 with its distal end to the right and the proximal end to the left. An optic tube 11 extends the full length of resectoscope 10 and is fitted with an ocular 13 at its proximal end. The optic tube 11 in turn is inserted into an elongated guide tube 15 rigidly affixed to a distal pipe 16. A carriage 17 is mounted displaceably on guide tube 15 for movement in the longitudinal direction of the instrument and carries a high-frequency cutting electrode 18 with a cutting loop 19 at its distal end. A stop 14 is immovably mounted on the resectoscope and is joined by links 28 to carriage 17, the links typically being urged apart by a compression coil spring 29.

Handles 21 extend in opposite directions from carriage 17 and can be gripped to longitudinally displace carriage 17 along guide tube 15. A grip component comprising a thumb ring 20 is mounted on stop 14 laterally away from the resectoscope 10 to be used in conjunction with handles 21 mounted on the carriage 17. Thumb ring 20 is an annular member having a through passage with at least one of the ends of that passage forming a thumb insertion aperture, the ring being shown with one of its apertures 22 facing the observer. The thumb ring is attached to a bracket 24, which is connected to stop 14 and thus to resectoscope 10. The attachment of ring 20 to bracket 24 is made at an affixation site 23 on the distal side of the ring so that the ring is rotatable about an axis parallel with the longitudinal axis of the instrument.

In operation, the surgeon or other operator inserts a thumb of one hand through the ring and engages one or both of handles 21 with one or more other fingers of the same hand. By moving the thumb and fingers together, carriage 17 is moved toward stop 14, thus moving the loop in the proximal direction and performing the cutting operation. When the thumb and fingers of the hand are moved apart, carriage 17 is moved away from stop 14, aided by spring 29, to prepare for another cut. As will be recognized, when the thumb is inserted into the ring, the thumbnail normally faces in the proximal direction and the top surface of the thumb adjacent the nail is in contact with the inner surface of the proximal side of the ring.

Thumb ring 20 of the invention has a concave rest surface 25 on the inner surface of the proximal side of the ring, opposite affixation site 23. Rest surface 25 approximately follows the shape of the surface of a cylinder whose axis 30 forms an acute angle with the axis 31 of ring 20. Rest surface 25 is oriented in such manner that there is the largest possible contact area of the ring with the top surface of the thumb.

Figure 2:
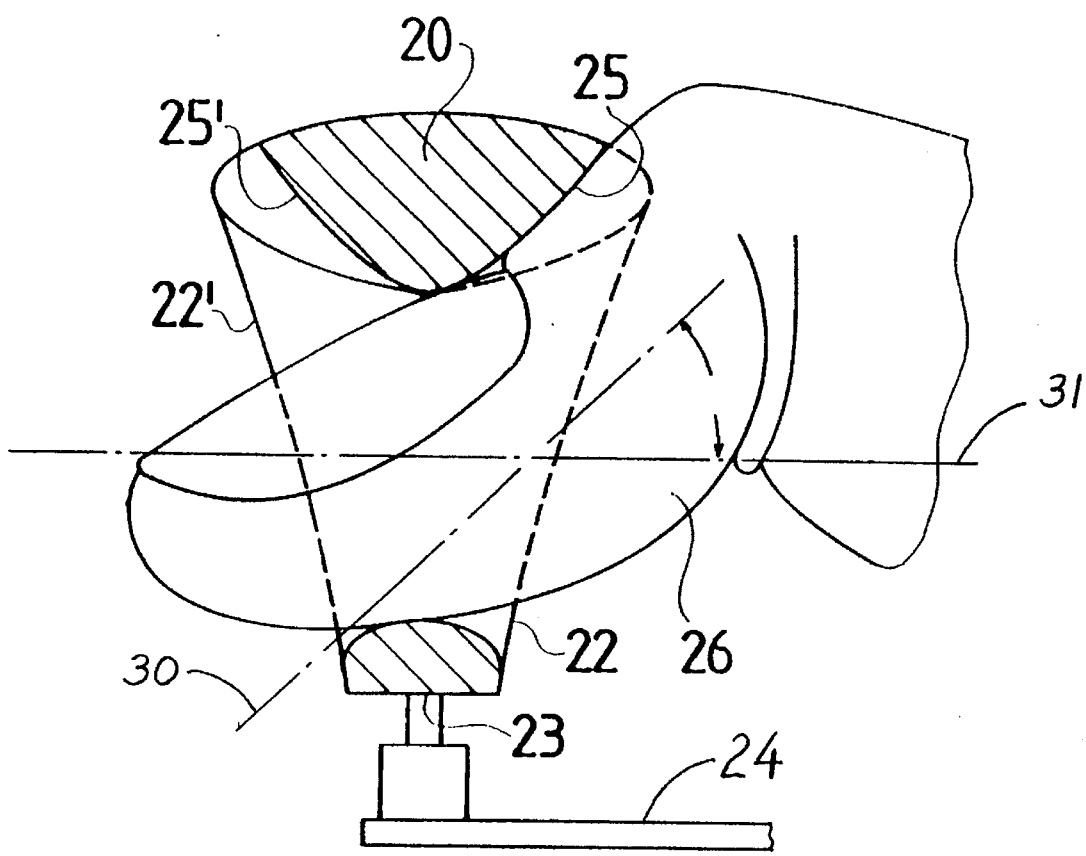
FIG. 2 is a longitudinal section through a thumb ring in accordance with the invention also showing a thumb inserted therethrough.

As best shown in FIG. 2, the rest surface 25 is not restricted to a single insertion aperture 22 of the thumb ring 20. Indeed, two rest surfaces may be provided, one adjacent each aperture.

This feature is made clear in the sectional diagram of FIG. 2. A thumb ring 20 is shown with apertures 22 and 22' at opposite ends of the central passage through annular ring 20. Each aperture 22, 22' has an associated concave rest surface 25, 25' on the inner surface of the ring on the side of the ring opposite the affixation site 23. A thumb 26 inserted through insertion aperture 22 into thumb ring 20 is shown in FIG. 2.

The thumb rests with its comparatively insensitive lower side on the lower ring area, while the thumb top side in the especially sensitive transition zone between thumb nail and skin rests against the rest surface 25. The pressure exerted by the thumb ring 20 on the thumb top side therefore is uniformly distributed over a large area of the top side of the thumb. Painful pressures are avoided especially when, as shown, the rest surface 25 is slightly convex in the direction of the ring axis.

The diameter of the cylinder of whose surface is followed by surface 25 or 25' is preferably selected to approximate that of the distal joint of the thumb to maximize the surface contact area and can be varied slightly, as can the diameter of the ring itself, to accomodate thumbs of different sizes. As illustrated in FIG. 2, surface 25 is preferably not exactly cylindrical. Better contact is made if surface 25, 25' is slightly convex relative to the cylindrical axis, i.e., if it bulges slightly as does the top side of the thumb.

What is claimed is:

1. A thumb ring for an endoscopic instrument comprising a generally annular body having a passage therethrough with a first central axis, said passage having two ends, at least one of said ends comprising an insertion aperture for receiving a thumb of an operator into said passage, the insertion aperture having a second central axis;

means attached to a fixation site at an attachment side of said body for mounting said body on an endoscopic instrument so that said body is rotatable about an axis parallel with a longitudinal axis of the instrument; and a concave rest surface formed on said insertion aperture at an edge distal to said attachment side of said body such that said second central axis forms an acute angle with said first central axis, said concave rest surface having a central convex bulge portion shaped and configured to fit the contours of the top surface of the operator's thumb in an area between the cuticle and the distal most joint of the thumb thereby providing a large surface area of contact with the thumb.

2. A thumb ring according to claim 1 wherein both ends of said passage are formed as insertion apertures, and wherein a concave rest surface is formed on each said aperture such that the central axis of each said aperture forms an acute angle with said first central axis, each said rest surface having a central convex bulge portion shaped and configured to fit the contours of the top surface of the operator's thumb in an area between the cuticle and the distal most joint of the thumb thereby providing a large surface area of contact with the thumb.

\* \* \* \* \*